United States Patent [19]
Van Noy et al.

[11] Patent Number: 5,947,976
[45] Date of Patent: Sep. 7, 1999

[54] ASYMMETRIC INTRAOCULAR LENS INJECTION CARTRIDGE

[75] Inventors: Stephen J. Van Noy; Kyle Brown; David A. Downer, all of Fort Worth; David Eister, Mansfield; Lars D. Jensen, Arlington, all of Tex.

[73] Assignee: Alcon Laboratories, Inc.

[21] Appl. No.: 09/089,284

[22] Filed: Jun. 2, 1998

[51] Int. Cl.⁶ .................................................. A61F 9/00
[52] U.S. Cl. ..................... 606/107; 606/106; 606/108; 623/6; 623/4; 604/96
[58] Field of Search .................... 606/107, 106, 606/108; 623/6, 4; 604/96

[56] References Cited

U.S. PATENT DOCUMENTS

| | | |
|---|---|---|
| 4,573,998 | 3/1986 | Mazzocco . |
| 4,681,102 | 7/1987 | Bartell . |
| 4,747,404 | 5/1988 | Jampel et al. . |
| 4,834,094 | 5/1989 | Patton et al. . |
| 4,836,201 | 6/1989 | Patton et al. . |
| 4,919,130 | 4/1990 | Stoy et al. . |
| 5,007,913 | 4/1991 | Dulebohn et al. . |
| 5,190,552 | 3/1993 | Kelman . |
| 5,275,604 | 1/1994 | Rheinish et al. . |
| 5,304,182 | 4/1994 | Rheinish et al. ................. 606/107 |
| 5,494,484 | 2/1996 | Feingold . |
| 5,499,987 | 3/1996 | Feingold . |
| 5,616,148 | 4/1997 | Eagles et al. . |
| 5,620,450 | 4/1997 | Eagles et al. . |
| 5,653,715 | 8/1997 | Reich et al. . |
| 5,653,753 | 8/1997 | Brady et al. . |
| 5,716,364 | 2/1998 | Makker et al. ................... 606/107 |
| 5,728,102 | 3/1998 | Feingold et al. ................. 606/107 |
| 5,735,858 | 4/1998 | Makker et al. . |
| 5,803,925 | 9/1998 | Yang et al. ...................... 606/107 |
| 5,810,834 | 9/1998 | Heyman .......................... 606/107 |

FOREIGN PATENT DOCUMENTS

| | | |
|---|---|---|
| 2224214A | 5/1990 | United Kingdom . |
| WO 96/29956 | 10/1996 | WIPO . |
| WO 98/15244 | 4/1998 | WIPO . |

*Primary Examiner*—Michael Buiz
*Assistant Examiner*—(Jackie) Tan-Uyen T. Ho
*Attorney, Agent, or Firm*—Jeffrey S. Schira

[57] ABSTRACT

A lens injector cartridge having an asymmetric bore. The asymmetric bore initiates the folding of the lens on one side only, thereby reducing the amount of energy imparted to the lens and the potential for damage to the lens. The gentle folding of the lens also assists in positioning the travel of the haptics down the bore, thereby reducing the potential for damage to the haptics.

10 Claims, 6 Drawing Sheets

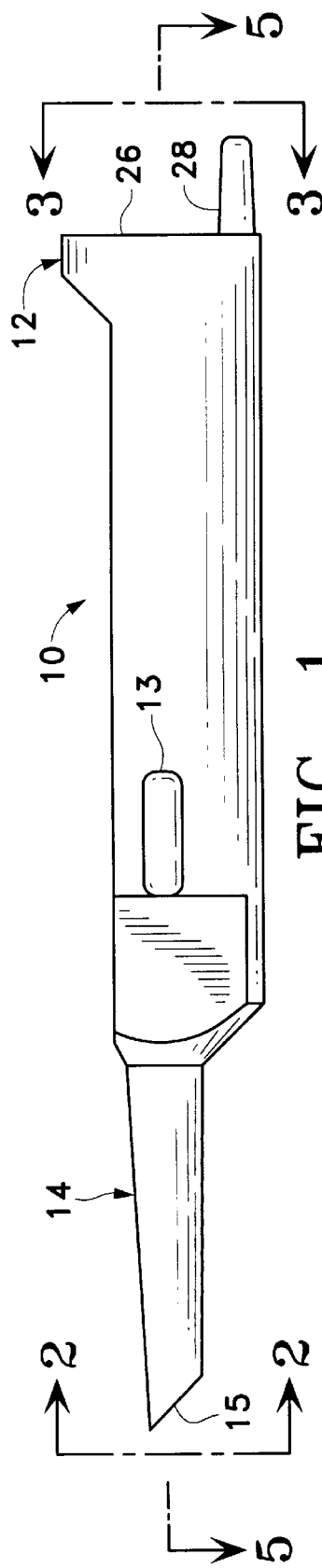
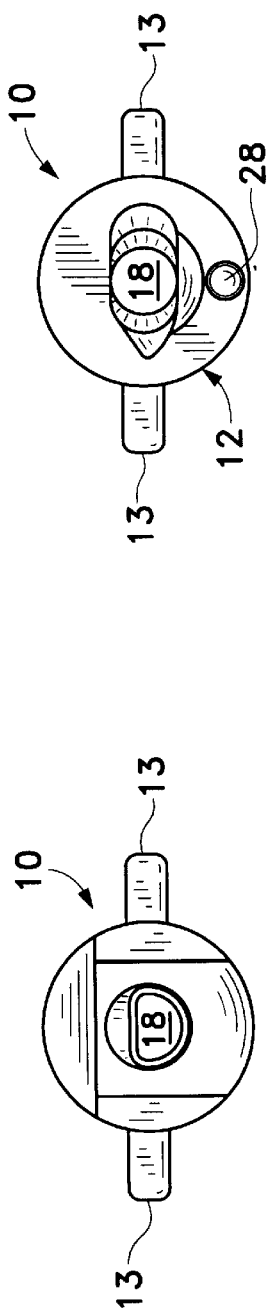
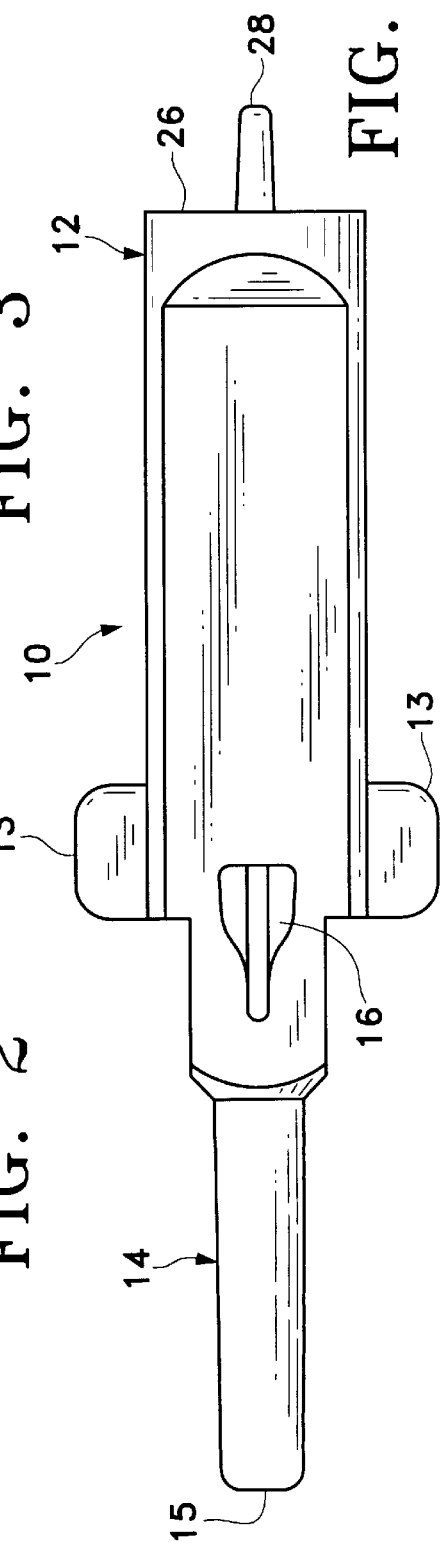

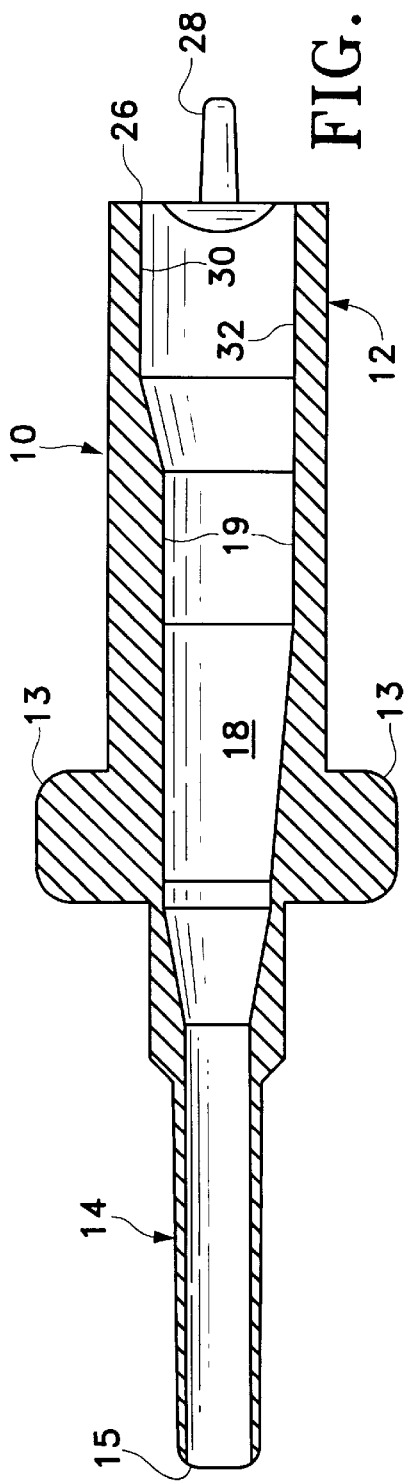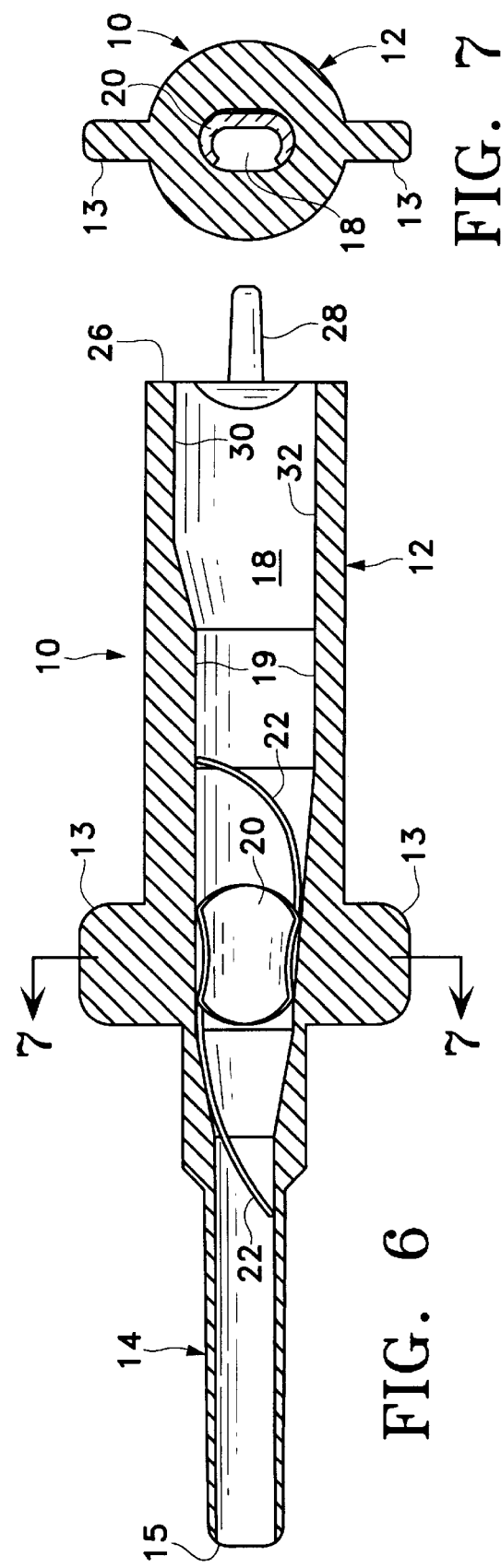

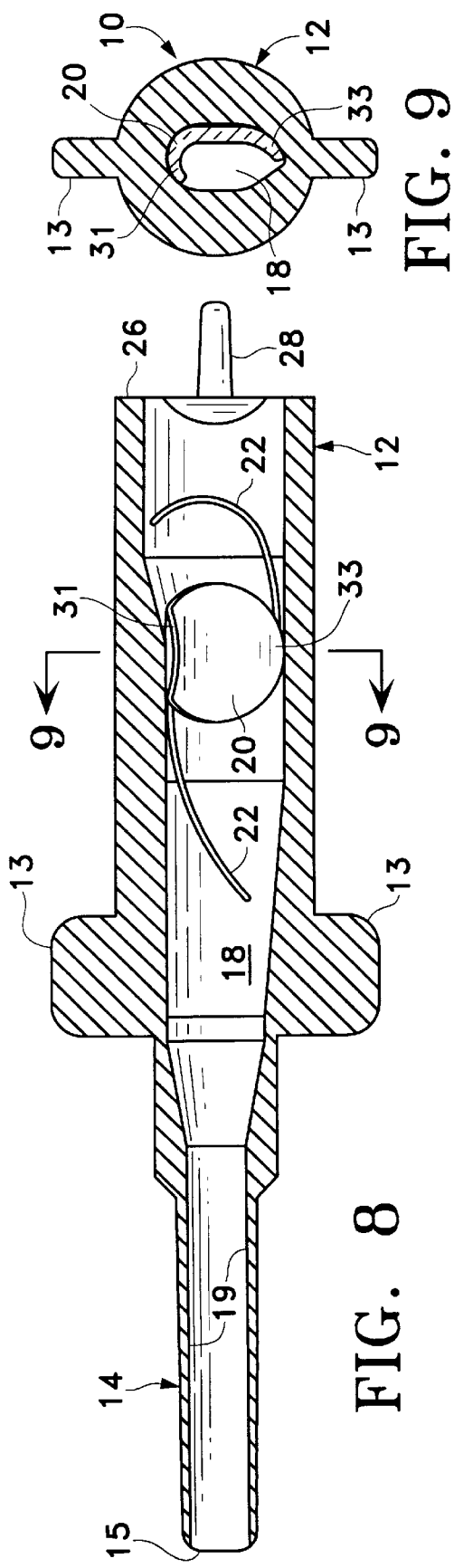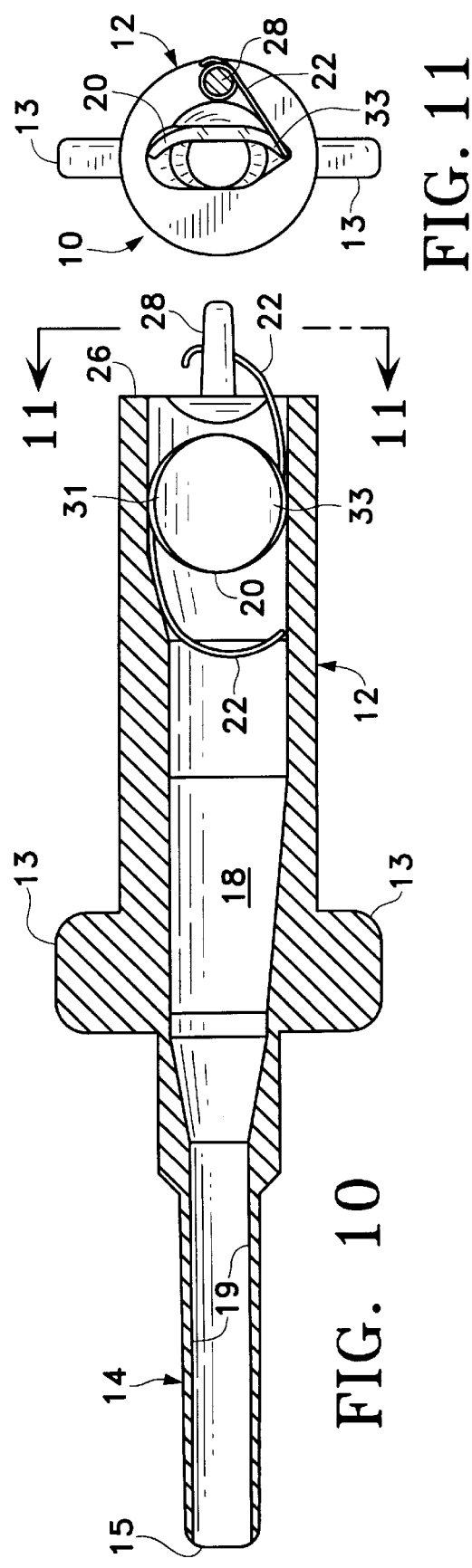

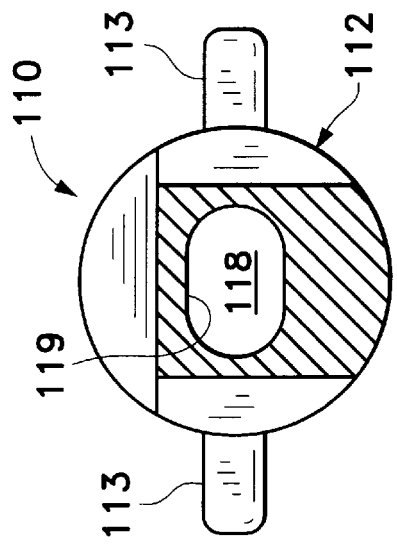
FIG. 13
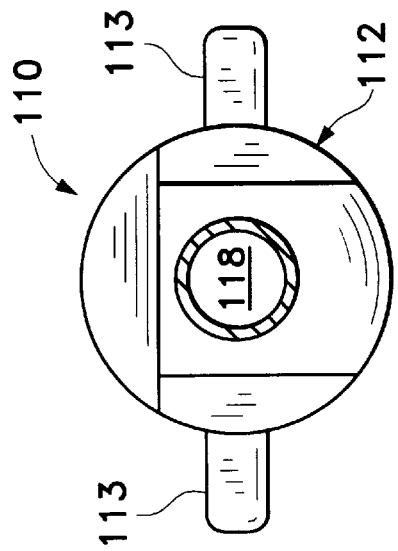
FIG. 14
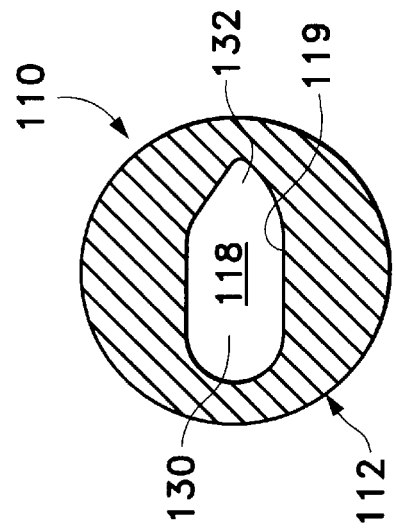
FIG. 15
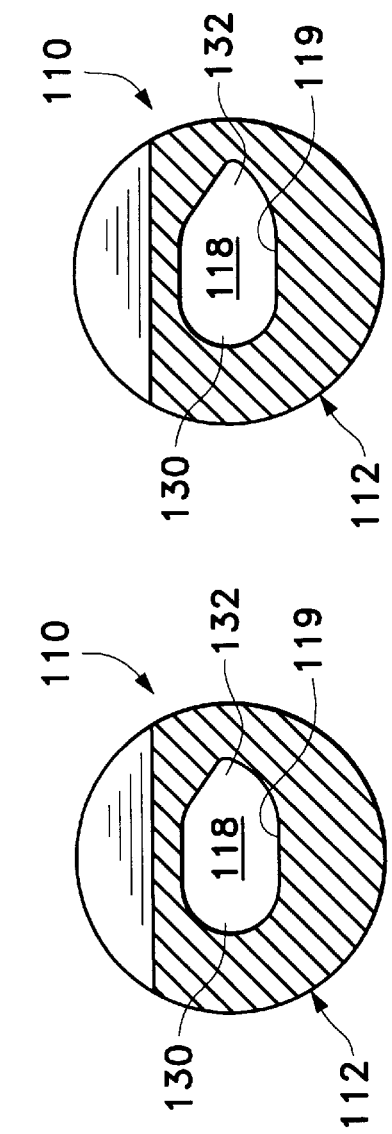
FIG. 16
FIG. 17

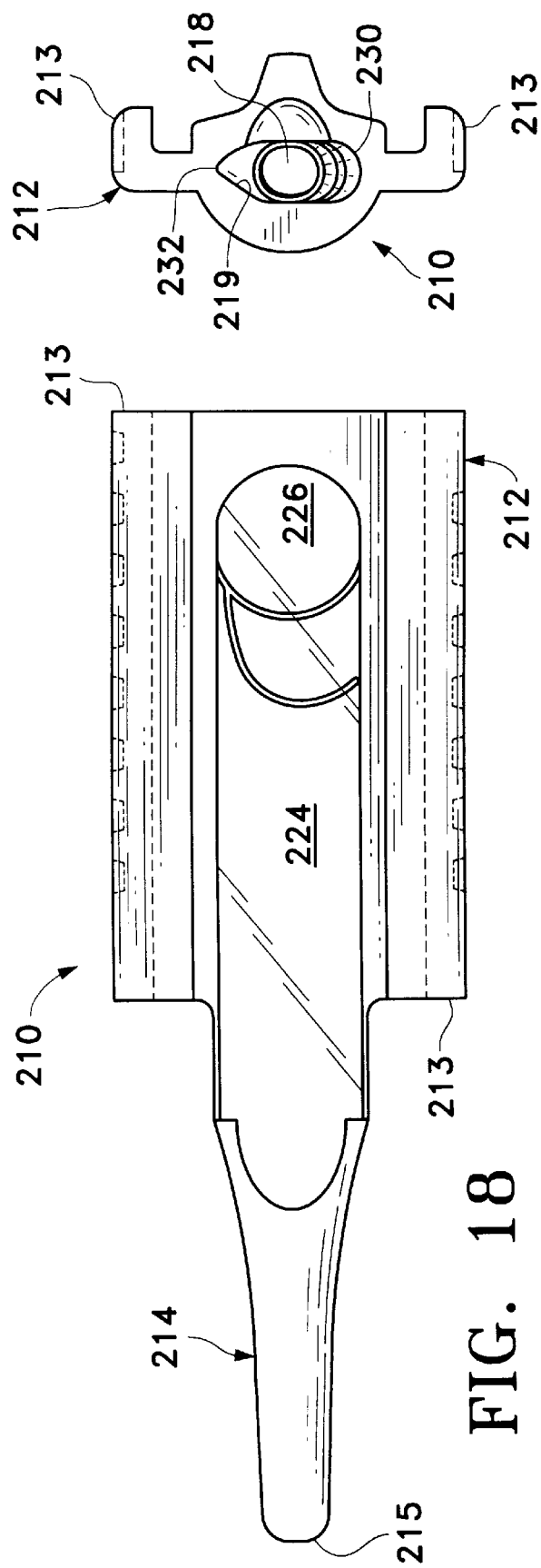
FIG. 18
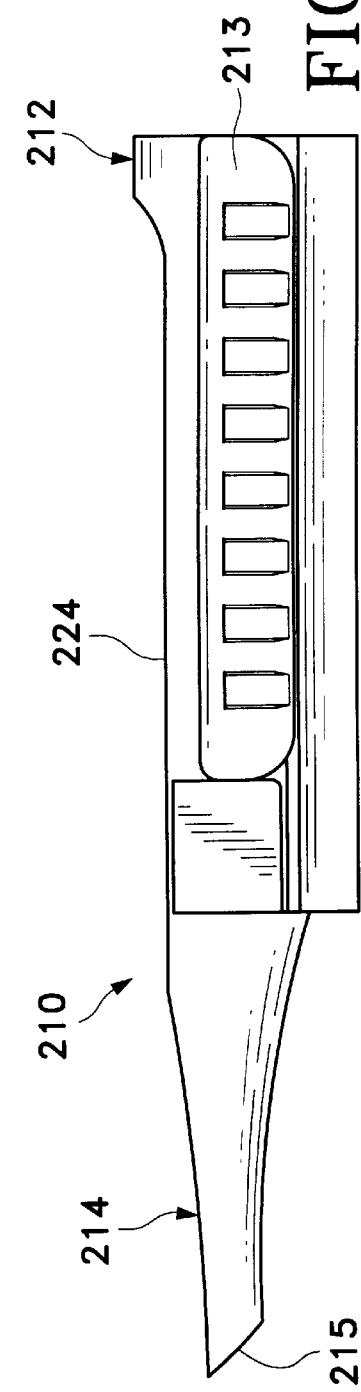
FIG. 19
FIG. 20

ASYMMETRIC INTRAOCULAR LENS INJECTION CARTRIDGE

BACKGROUND OF THE INVENTION

The human eye in its simplest terms functions to provide vision by transmitting and refracting light through a clear outer portion called the cornea, and further focusing the image by way of the lens onto the retina at the back of the eye. The quality of the focused image depends on many factors including the size, shape and length of the eye, and the shape and transparency of the cornea and lens.

When trauma, age or disease cause the lens to become less transparent, vision deteriorates because of the diminished light which can be transmitted to the retina. This deficiency in the lens of the eye is medically known as a cataract. The treatment for this condition is surgical removal of the lens and implantation of an artificial lens or IOL.

While early IOLs were made from hard plastic, such as polymethylmethacrylate (PMMA), soft, foldable IOLs made from silicone, soft acrylics and hydrogels have become increasingly popular because of the ability to fold or roll these soft lenses and insert them through a smaller incision. Several methods of rolling or folding the lenses are used. One popular method is an injector cartridge that folds the lenses and provides a relatively small diameter lumen through which the lens may be pushed into the eye, usually by a soft tip plunger. The most commonly used injector cartridge design is illustrated in Bartell U.S. Pat. No. 4,681,102, the entire contents of which is incorporated herein by reference, and includes a split, longitudinally hinged cartridge. Similar designs are illustrated in Feingold U.S. Pat. Nos. 5,494,484 and 5,499,987 and Eagles, et al. U.S. Pat. Nos. 5,616,148 and 5,620,450 al.), the entire contents of which are incorporated herein by reference. In an attempt to avoid the claims of U.S. Pat. No. 4,681,102, several solid cartridges have been investigated, see for example Rheinish, et al. U.S. Pat. Nos. 5,275,604 and Reich, et al., U.S. Pat. No. 5,653,715 the entire contents of which are incorporated herein by reference.

These prior art cartridges all have a smooth, round or elliptical bore that is symmetric about the longitudinal axis. While a smooth round bore works well with elastic materials such as silicones and hydrogel, viscoelastic materials such as soft acrylics do not roll or fold as easily, and preferably are rolled or folded more gradually to help prevent damage to the optic and/or haptic.

Accordingly, a need continues to exist for an IOL injector cartridge that gently folds the IOL.

BRIEF SUMMARY OF THE INVENTION

The present invention improves upon prior art injector cartridges by providing a cartridge having an asymmetric bore. The asymmetric bore initiates the folding of the lens on one side only, thereby reducing the amount of energy imparted to the lens and the potential for damage to the lens. The gentle folding of the lens also assists in positioning the travel of the haptics down the bore, thereby reducing the potential for damage to the haptics.

It is accordingly an object of the present invention to provide a lens injector cartridge having an asymmetric bore.

It is a further object of the present invention to provide a lens injector cartridge that gently folds the lens.

It is a further object of the present invention to provide a lens injector cartridge that minimizes the potential for damage to the optic and/or the haptics.

Other objects, features and advantages of the present invention will become apparent with reference to the drawings, and the following description of the drawings and claims.

BRIEF DESCRIPTION OF THE DRAWINGS

FIG. 1 is a side elevational view of a first embodiment of the intraocular lens injection cartridge of the present invention.

FIG. 2 is a front elevational view of a first embodiment of the intraocular lens injection cartridge of the present invention.

FIG. 3 is a rear elevational view of a first embodiment of the intraocular lens injection cartridge of the present invention.

FIG. 4 is a top plan view of a first embodiment of the intraocular lens injection cartridge of the present invention.

FIG. 5 is a longitudinal cross-sectional view of a first embodiment of the intraocular lens injection cartridge of the present invention taken along line 5—5 in FIG. 1.

FIG. 6 is a longitudinal cross-sectional view of a first embodiment of the intraocular lens injection cartridge of the present invention similar to FIG. 5 illustrating an intraocular lens partially folded.

FIG. 7 is a tansverse cross-sectional view of a first embodiment of the intraocular lens injection cartridge of the present invention taken along line 7—7 in FIG. 6.

FIG. 8 is a longitudinal cross-sectional view of a first embodiment of the intraocular lens injection cartridge of the present invention similar to FIGS. 5 and 6 illustrating the initial folding of one side of an intraocular lens.

FIG. 9 is a transverse cross-sectional view of a first embodiment of the intraocular lens injection cartridge of the present invention similar to FIG. 7 but taken along line 9—9 in FIG. 8.

FIG. 10 is a longitudinal cross-sectional view of a first embodiment of the intraocular lens injection cartridge of the present invention similar to FIGS. 5, 6 and 8 illustrating the initial position of an intraocular lens in the bore.

FIG. 11 is a rear elevational view of a first embodiment of the intraocular lens injection cartridge of the present invention similar to FIG. 3 but illustrating the initial position of an intraocular lens in the bore.

FIG. 13 is a transverse cross-sectional view of the bore that may be used with the present invention taken along line 13—13 in FIG. 12.

FIG. 14 is a transverse cross-sectional view of the bore that may be used with the present invention taken along line 14—14 in FIG. 12.

FIG. 15 is a transverse cross-sectional view of the bore that may be used with the present invention taken along line 15—15 in FIG. 12.

FIG. 16 is a transverse cross-sectional view of the bore that may be used with the present invention taken along line 16—16 in FIG. 12.

FIG. 17 is a transverse cross-sectional view of the bore that may be used with the present invention taken along line 17—17 in FIG. 12.

FIG. 18 is a top plan view of a third embodiment of the intraocular lens injection cartridge of the present invention.

FIG. 19 is a rear elevational view of the third embodiment of the intraocular lens injection cartridge of the present invention illustrated in FIG. 18.

FIG. 20 is a side elevational view of the third embodiment of the intraocular lens injection cartridge of the present invention.

DETAILED DESCRIPTION OF THE INVENTION

Figure 12:
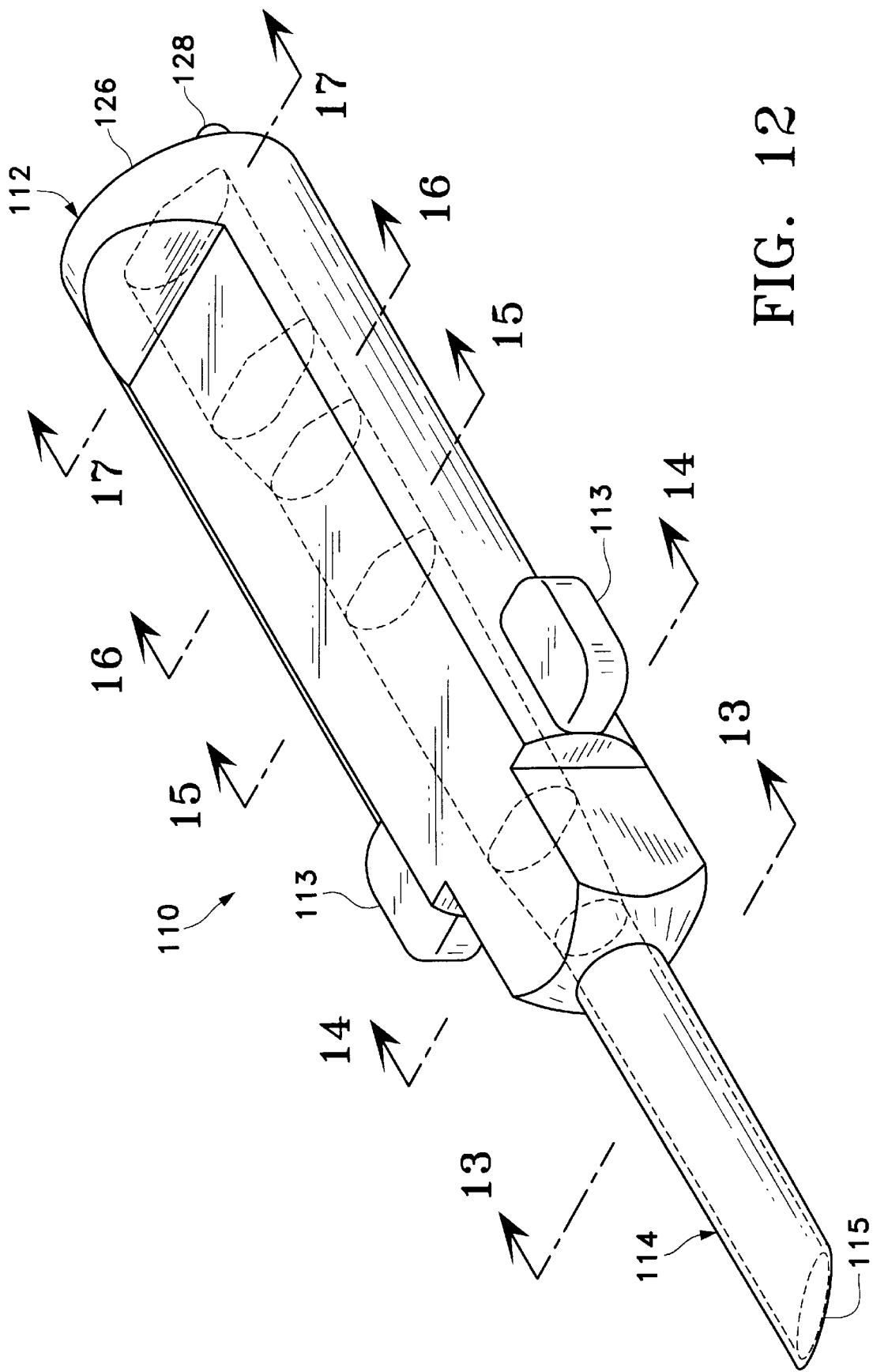
FIG. 12 is a perspective view of a second embodiment of the intraocular lens injection cartridge of the present invention showing the bore in shadow line.

As best seen in FIGS. 1, 4, 12, 18 and 20 intraocular lens injector cartridge 10, 110 and 210 of the present invention generally has tubular body 12, 112 and 212 and injection nozzle 14, 114 and 214. Cartridge 10, 110 and 210 preferably is molded as a single piece from any suitable thermoplastic, such as polypropylene, and the thermoplastic may contain a lubricity enhancing agent such as those disclosed in U.S. Pat. No. 5,716,364, the entire contents of which is incorporated herein by reference. Alternatively, cartridge 10, 110 and 210 may be made from stainless steel or titanium. Nozzle 14, 114 and 214 preferably is round, oval or elliptical in cross-section and has a cross-sectional area of between around 1.5 mm$^2$ to around 6.5 mm$^2$. Distal tip 15, 115 and 215 of nozzle 14, 114 and 214 preferably is rounded on the interior and exterior.

As best seen in FIGS. 4, 12, 18 and 19, body 12, 112 and 212 preferably contain grips 13, 113 and 213 that allow easier manipulation of cartridge 10, 110 and 210 and provide a mechanism to lock cartridge 10, 110 and 210 in the injection handpiece (not shown). As best seen in FIG. 4, body 12 may contain opening 16, that communicates with bore 18. Opening 16 allows visualization of IOL 20 and haptics 22 as IOL 20 enters nozzle 14. Alternatively, as shown in the second embodiment illustrated in FIG. 12, body 112 may be solid and contain no opening or, as shown in the third embodiment illustrated in FIG. 18, body 212 may contain solid, transparent window 224 that allows for visualization of the IOL in bore 218. In addition, window 224 may contain outline 226 of an IOL that indicates correct orientation of the IOL in cartridge 210. In the embodiments illustrated in FIGS. 1, 4 and 12, proximal end 26 and 126 of bodies 12 and 112, respectively, may contain peg 28 and 128 around which haptic 22 may be wrapped, as illustrated in FIG. 10. Such an orientation of haptic 22 helps prevent haptic 22 from being caught by the mechanism driving IOL 20 down bore 18 or 118.

As best seen in FIGS. 5–17 and 19, bore 18, 118 and 218 is asymmetric, rounded on one side 30, 130 and 230 and ramped on the other side 32, 132 and 232 near proximal end 26, 126 and 226, tapering into an oval or circle near nozzle 14, 114 and 214. As best seen in FIGS. 6–11, ramped side 32 holds edge 33 of IOL 20 relatively flat as IOL 20 is pushed down bore 18 while rounded side 30 of bore 18 rolls or folds edge 31 of IOL 20. Gently rounding off ramped side 32 near nozzle 14 allows side 32 to roll or fold edge 33 after edge 31 has been rolled, as shown in FIGS. 6 and 7. Such an asymmetric construction slowly folds one side of IOL 20 at a time and is particularly advantageous when IOL 20 is made from a viscoelastic material such as a soft acrylic, because such gentle folding allows the material to flow into the folded shape with less potential for damage to IOL 20. In addition, the asymmetric folding action of the present invention helps prevent haptics 22 from becoming trapped or pinned within bore 18 by IOL 20 and being damaged.

In order to facilitate further the movement of IOL 20 down bore 18, 118 and 218, interior surface 19, 119 and 219 of bore 18, 118 and 218 may be coated with a lubricous coating such as those described in U.S. Pat. Nos. 4,487,865, 4,500,676, 4,663,233, 4,801,475, 4,959,074, 5,023,114 and 5,037,677, the entire contents of which are incorporated herein by reference. Bore 18, 118 and 218 may also be coated by any commercially available medical grade viscoelastic, such as VISCOAT® viscoelastic available from Alcon Laboratories, Inc., Fort Worth, Texas. The inventors have also found that texturing interior surface 19, 119 and 219 also assists in the movement of IOL 20 down bore 18, 118 and 218 by minimizing the amount of surface contact between interior surface 19, 119 or 219 and IOL 20 and by entrapping any viscoelastic agent between interior surface 19, 119 or 219 and IOL 20. For example, a surface roughness of greater than 0.45 microns RMS may be used. Such a finish can be generated by a two step process incorporating an initial random pattern texture by sandblasting or acid etching followed by a specific directional polish along the longitudinal axis of bore 18, 118 or 218 in order to achieve a cropped or plateau effect.

While certain embodiments of the present invention have been described above, these descriptions are given for purposes of illustration and explanation. Variations, changes, modifications and departures from the systems and methods disclosed above may be adopted without departure from the scope or spirit of the present invention.

We claim:

1. An intraocular lens injector cartridge, comprising:
    a) a body having a bore that has an asymmetric transverse cross section; and
    b) an injection nozzle integrally formed with the body, the nozzle having a bore that communicates with the bore in the body.

2. The cartridge of claim 1, wherein the bore is rounded on one side and ramped on the other side.

3. The cartridge of claim 1, wherein the bore has a textured interior surface.

4. The cartridge of claim 1, wherein the body contains a window.

5. The cartridge of claim 4, wherein the window contains an orientation outline.

6. A method of folding an intraocular lens, comprising the steps of:
    a) providing a lens injector cartridge having a body with a bore that has an asymmetric transverse cross section; and
    b) pushing the intraocular lens down the bore so that a first edge of the intraocular lens is folded while a second edge of the intraocular lens opposite the first edge is held relatively flat.

7. The method of claim 6, wherein the step of pushing the intraocular lens down the bore includes visualizing the intraocular lens in a window having an orientation outline.

8. The method of claim 6, wherein the bore is rounded on one side and ramped on the other side.

9. The method of claim 6, wherein the bore has a textured interior surface.

10. The cartridge of claim 1 further comprising a peg attached to a proximal end of the body.

* * * * *